US007952081B2

(12) United States Patent
Shimada et al.

(10) Patent No.: US 7,952,081 B2
(45) Date of Patent: May 31, 2011

(54) DEVICE FOR DETERMINING AIM POSITION OF CHARGED PARTICLE BEAM, METHOD OF USING THE DEVICE, AND TREATMENT DEVICE EMPLOYING DEVICE FOR DETERMINING AIM POSITION

(75) Inventors: Hirofumi Shimada, Takasaki (JP); Takashi Nakano, Maebashi (JP); Takuro Sakai, Takasaki (JP); Kazuo Arakawa, Takasaki (JP); Mitsuhiro Fukuda, Takasaki (JP); Masakazu Oikawa, Takasaki (JP); Takahiro Satoh, Takasaki (JP); Takashi Agematsu, Takasaki (JP); Ken Yusa, Maebashi (JP); Hiroyuki Katoh, Maebashi (JP); Shoji Kishi, Maebashi (JP); Taku Sato, Maebashi (JP); Yasushi Horiuchi, Maebashi (JP)

(73) Assignees: National University Corporation Gunma University, Gunma (JP); Japan Atomic Energy Agency, Ibaraki (JP)

( * ) Notice: Subject to any disclaimer, the term of this patent is extended or adjusted under 35 U.S.C. 154(b) by 79 days.

(21) Appl. No.: 12/160,420

(22) PCT Filed: Jan. 12, 2007

(86) PCT No.: PCT/JP2007/050347
§ 371 (c)(1),
(2), (4) Date: Aug. 28, 2009

(87) PCT Pub. No.: WO2007/080981
PCT Pub. Date: Jul. 19, 2007

(65) Prior Publication Data
US 2010/0163726 A1    Jul. 1, 2010

(30) Foreign Application Priority Data

Jan. 12, 2006    (JP) ................. 2006-004794

(51) Int. Cl.
*G21K 5/00* (2006.01)
(52) U.S. Cl. .......... 250/491.1; 250/492.1; 600/1; 607/1; 607/141
(58) Field of Classification Search ............... 250/491.1, 250/492.1, 492.3, 493.1; 600/1, 2; 607/1, 607/2, 3, 141
See application file for complete search history.

(56) References Cited

U.S. PATENT DOCUMENTS
2003/0071966 A1*    4/2003    Matsumoto ................... 351/206
(Continued)

FOREIGN PATENT DOCUMENTS
JP    01-126257    8/1989
(Continued)

*Primary Examiner* — Robert Kim
*Assistant Examiner* — Nicole Ippolito Rausch
(74) *Attorney, Agent, or Firm* — Hogan Lovells US LLP

(57) ABSTRACT

A subject is imaged for treatment of the subject such as an eye to be inspected, while irradiating a charged particle beam on the eye, so that an aim position of a charged particle beam for treatment can be determined.

The device for determining an aim position of a charged particle beam includes a range adjuster 14 that adjusts an irradiation position, in a depth direction of the eye, of a charged particle beam irradiated from a charged particle beam source, a mirror 18 that transmits or passes the position determining charged particle beam and reflects an emitted light emitted from a region of the eye on which the charged particle beam is irradiated and an emitted light emitted, due to an irradiated of an excitation light, from a region including the region of the eye on which the position determining charged particle beam, toward the outside of the axis of the charged particle beam, and an eyeground imaging device 24 that is arranged at a position where the emitted lights reflected from the mirror are incident and images the region including the region of the eye on which the charged particle beam is irradiated by causing the emitted lights to be incident, so that it allows to determine an aim position of a charged particle beam for treatment based on a imaged image.

14 Claims, 7 Drawing Sheets

U.S. PATENT DOCUMENTS

2003/0136924 A1* 7/2003 Kraft et al. .............. 250/492.3
2007/0181815 A1* 8/2007 Ebstein .................. 250/370.11

FOREIGN PATENT DOCUMENTS

| | | |
|---|---|---|
| JP | 05-007251 | 2/1993 |
| JP | 09-173376 | 7/1997 |
| JP | 09-192106 | 7/1997 |
| JP | 10-015087 | 1/1998 |
| JP | 2000-237168 | 9/2000 |
| JP | 2002-034919 | 2/2002 |
| JP | 2002-200182 | 7/2002 |
| JP | 2003-516830 | 5/2003 |
| JP | 2004-097471 | 4/2004 |
| JP | 2004192931 A | 7/2004 |
| JP | 2005-021366 | 1/2005 |
| WO | WO 2004/065923 A1 | 8/2004 |
| WO | 2006/005059 | 1/2006 |

* cited by examiner

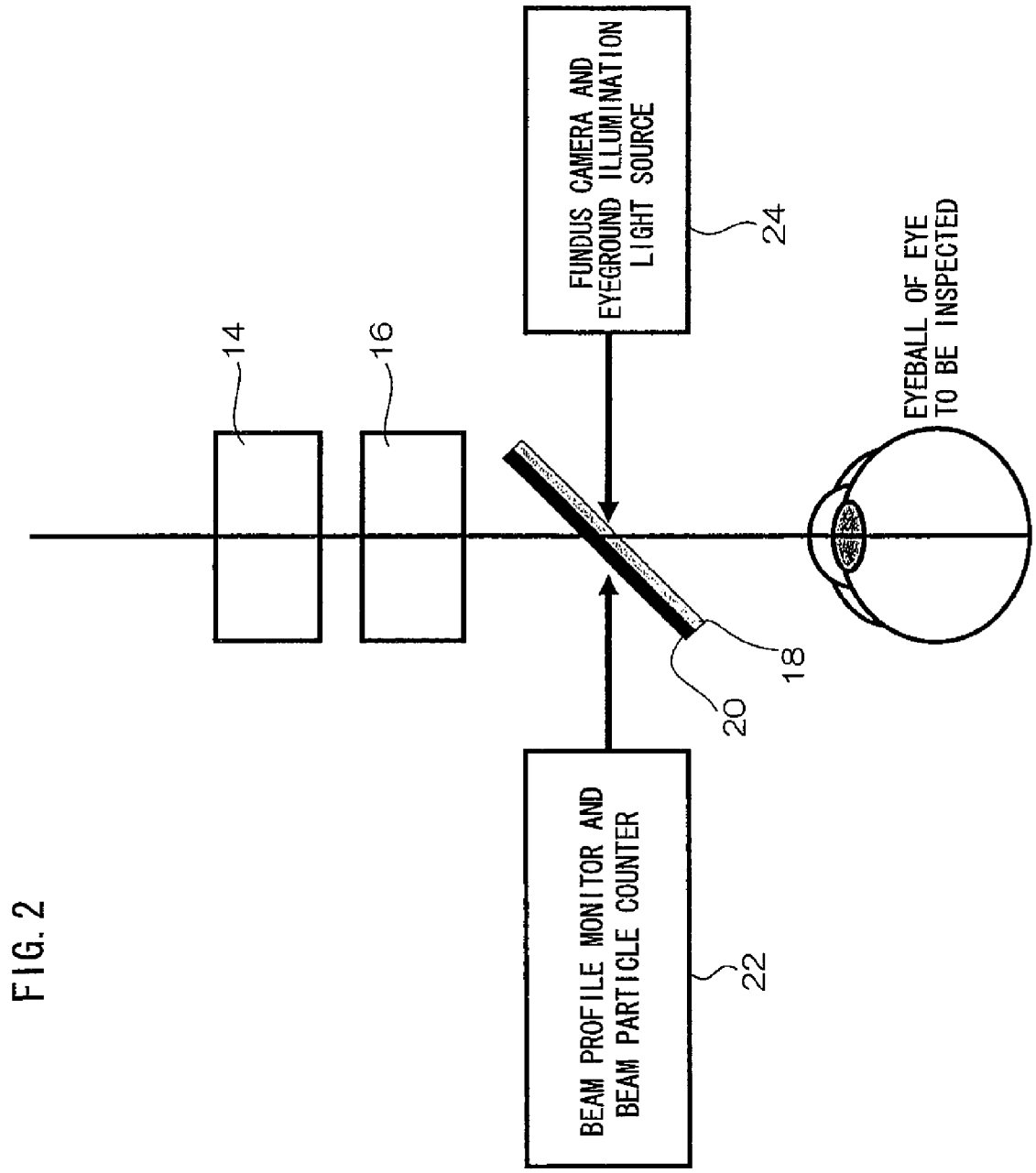

FLUORESCEIN FUNDUS ANGIOGRAPHIC
IMAGE BY EXCITATION LIGHT SOURCE

FLUORESCEIN FUNDUS ANGIOGRAPHIC IMAGE BY PRELIMINARY DIAGNOSIS

FLUORESCEIN FUNDUS ANGIOGRAPHIC IMAGE BY EXCITATION LIGHT SOURCE

FLUORESCEIN FUNDUS ANGIOGRAPHIC IMAGE BY
DEPTH POSITION DETERMINING BEAM (Φ1 to 10mm)

FLUORESCEIN FUNDUS ANGIOGRAPHIC
IMAGE BY EXCITATION LIGHT SOURCE

DEVICE FOR DETERMINING AIM POSITION OF CHARGED PARTICLE BEAM, METHOD OF USING THE DEVICE, AND TREATMENT DEVICE EMPLOYING DEVICE FOR DETERMINING AIM POSITION

CROSS-REFERENCE TO THE RELATED APPLICATIONS

This application is a national stage of international application No. PCT/JP2007/050347 filed Jan. 12, 2007, which also claims benefit of priority under 35 U.S.C. §119 to Japanese Patent Application No. 2006-004794 filed Jan. 12, 2006, the entire contents of which are incorporated herein by reference.

TECHNICAL FIELD

The prevent invention relates to a device for determining an aim position of a charged particle beam, a method of using the device, and a treatment device employing the device for determining an aim position. More particularly, the prevent invention relates to a device for determining an aim position of a charged particle beam that determines an aim position of a charged particle beam by irradiating the charged particle beam such as a carbon ion beam and excitation light on an eyeground of an eye to be inspected which is a subject and imaging an eyeground image, a method of using the device, and a treatment device employing the device for determining an aim position.

BACKGROUND ART

In a treatment using a charged particle beam, by using a characteristic of the charged particle beam in which energy centrality due to a Bragg peak is very high, a Bragg peak in which a width of the charged particle beam is spread to size of a field of irradiation is formed and is uniformly irradiated to a focus of disease, so that only an affected part can be efficiently irradiated.

On the other hand, a charged particle beam may be very narrowly focused by using a magnetic field or an electric field, and by using the focused charged particle beam, a beam may be precisely irradiated on a small region and the energy can be locally concentrated. As a technique of narrowly focusing a beam, a microbeam forming technique and a pencil beam forming technique is developed. By using these techniques in particle beam treatment, a technique for treatments of a small lesion, i.e., an ion micro surgery treatment technique or the like is theoretically possible. However, since a technique for aiming a deep irradiation position with a high precision and a technique for precisely confirming, in real time, a position which is irradiated for treatment, i.e., a position where a beam reaches are not present, the ion micro surgery treatment technique is not yet realized up to now.

An eyeground observing method using a conventional eyeground observation and diagnosis device employs a method of irradiating an eyeground using eyeground excitation light, intravenously injecting an eyeground fluorescence contrast agent into a patient as needed, and observing the fluorescence from the eyeground of a subject's eye. As the eyeground excitation light source, a visible light source for observing an eyeground and an eyeground blood vessel at a retina side of a cell than the retinal pigment epithelium and a near infrared light source for observing as well an eyeground blood vessel on a choroid side of the cell of the retinal pigment epithelium are used.

When the method is combined with a device which irradiates a charged particle beam on a small lesion such as an affected part of an eye and detects a generated signal, charged particles must be often deflected from a geometric arrangement. However, a very large deflecting electromagnet is required to deflect the charged particles, and the charged particle beam may not be easily deflected in the small area.

As conventional techniques related to the present invention, techniques disclosed in Patent Document 1 and Patent Document 2 are known.

Patent Document 1: Japanese Patent Application Laid-Open (JP-A) No. 2000-237168
Patent Document 2: JP-A No. 2002-034919

DISCLOSURE OF INVENTION

Problems to be Solved by the Invention

Therefore, it is disadvantageously difficult to precisely determine an aim position of a small region by using a conventional treatment device that uses a charged particle beam.

In order to cubically determine and check an aim position of a small lesion of a charged particle beam with respect to an eyeground while varying a depth of the charged particle beam, a predetermined depth and a position of an affected part of the eyeground must be observed while irradiating a charged particle beam for position determining. However, such technique is not yet implemented to a conventional device for determining an aim position.

The present invention is to solve this problem, and an object of the invention is to provide a device for determining an aim position of a charged particle beam that allows to determine the aim position of the charged particle beam for treatment by imaging a subject of treatment such as an subject's eye while irradiating a charged particle beam such as an ion beam on the subject, a method of using this device, and a treatment device employing this device for determining an aim position.

Means for Solving the Problem

In order to achieve the object, the present invention includes: an adjusting unit that adjusts an irradiation position, in a depth direction of a subject, of an irradiation position determining charged particle beam irradiated from a charged particle beam source; a reflecting unit that transmits or allows the position determining charged particle beam to pass, and reflects a first emitted light emitted from a region of the subject on which the position determining charged particle beam is irradiated and a second emitted light emitted, due to an irradiation of an excitation light, from a region including the region of the subject on which the position determining charged particle beam is irradiated, toward the outside of the axis of the charged particle beam; and an imaging unit that is arranged at a position where the first emitted light and the second emitted light reflected from the reflecting unit are incident and images the region including the region of the subject on which the position determining charged particle beam is irradiated by allowing incidence of the first emitted light and the second emitted light.

According to the invention, the reflecting unit that reflects the first emitted light emitted from the subject on which the position determining charged particle beam is irradiated and the second emitted light emitted, due to the irradiation of the excitation light, from the region including the region of the subject on which the position determining charged particle beam is irradiated, toward the outside of the axis of the charged particle beam is provided. Therefore, the axis of the charged particle beam does not interfere with an optical axis of the imaging unit which images the subject, and the region including the region of the subject on which the charged particle beam is irradiated may be imaged while irradiating the position determining charged particle beam. Based on the obtained image, an aim position of a charged particle beam for treatment may be determined.

The present may invention include a light emitter that is disposed in a path of the position determining charged particle beam irradiated on the subject, and emits light due to the irradiation of the position determining charged particle beam; and a detection unit that detects a position of the charged particle beam irradiated on the subject, on a plane orthogonal to the axis of the charged particle beam, based on the light emitted from the light emitter. In this manner, since, in addition to the irradiation position in the depth direction of the subject, i.e., a range of the charged particle beam, a position on a plane orthogonal to the axis of the charged particle beam irradiated on the subject may be checked, so that the aim position of the position determining charged particle beam may be three-dimensionally adjusted.

In the invention, the light emitter and the reflecting unit may be integrated in order to make it easy to handle the device for determining an aim position of a charged particle beam.

In the invention, a device for determining an aim position of a charged particle beam for an eyeground (eyeground device for determining an aim position) includes: an adjusting unit that adjusts an irradiation position, in a depth direction of an optic axis of an eye to be inspected which is a subject, of an irradiation position determining charged particle beam irradiated from a charged particle beam irradiation source, i.e., that adjusts a range of the position determining charged particle beam; a reflecting unit that transmits or allows the position determining charged particle beam to pass, and reflects a first emitted light emitted from a region of the eye on which the position determining charged particle beam is irradiated and a second emitted light emitted, due to an irradiation of an excitation light, from a region including the region of the eye on which the position determining charged particle beam is irradiated, toward the outside of the axis of the charged particle beam; and an imaging unit that is arranged at a position where the first emitted light and the second emitted light reflected from the reflecting unit are incident, and images the region including the region of the eye on which the position determining charged particle beam is irradiated by allowing incidence of the first emitted light and the second emitted light.

The eyeground device for determining an aim position may include a light emitter that is disposed in a path of the position determining charged particle beam irradiated on the eye, and emits light due to the irradiation of the position determining charged particle beam; and a detection unit that detects a position of the charged particle beam irradiated on the eye on a plane orthogonal to the axis of the beam, based on the emitted light emitted from the light emitter. The light emitter and the reflecting unit may be integrated.

In use of the eyeground position determining device, in a plurality of steps, an irradiation position along the direction of an optic axis of the eye of the charged particle beam, which is irradiated from the charged particle beam irradiation source, is adjusted by the adjusting unit in a direction from the sclera of the eyeground to the retina; the first emitted light emitted from the region of the eye on which the position determining charged particle beam is irradiated, to be incident to the imaging unit and imaging, in every step, the region including the region of the eye on which the position determining charged particle beam is irradiated; the irradiation position of the position determining charged particle beam to a targaposition is adjusted by the adjusting unit on the basis of an image obtained by the imaging; and the second emitted light reflected from the reflecting unit is made to be incident thereon and imaging the region including the region of the eye on which the position determining charged particle beam is irradiated to determine an aim position of a charged particle beam for treatment.

A standard position determining device according to the present invention may be applied to a treatment device using a charged particle beam. For example, the treatment device is configured as described below.

The treatment device includes: an adjusting unit that adjusts an irradiation position, in a depth direction of a subject, of an irradiation position determining charged particle beam irradiated from a charged particle beam source; a reflecting unit that transmits or allows the position determining charged particle beam to pass and reflects a first emitted light emitted from a region of the subject on which the position determining charged particle beam is irradiated and a second emitted light emitted, due to an irradiation of an excitation light, from a region including the region of the subject on which the position determining charged particle beam is irradiated, toward the outside of the axis of the charged particle beam; and an imaging unit that is arranged at a position where the first emitted light and the second emitted light reflected from the reflecting unit are incident and images a region including the region of the subject on which the position determining charged particle beam is irradiated by allowing incidence of the first emitted light and the second emitted light, wherein the adjusting unit adjusts, in a plurality of steps, an irradiation position, along a depth direction of a subject, of the position determining charged particle beam irradiated from the charged particle beam irradiation source, the imaging unit images, in every step, a region including the region of the subject on which the position determining charged particle beam is irradiated by allowing the first emitted light emitted from the part of the subject on which the position determining charged particle beam is irradiated to be incident on the imaging unit, the adjusting unit adjusts the irradiation position of the position determining charged particle beam toward a target position on the basis of an image obtained by the imaging, the imaging unit images, by allowing the second emitted light reflected from the reflecting unit to be incident thereon, the region including the region of the subject on which the position determining charged particle beam is irradiated to determine an aim position of a charged particle beam for treatment, and the irradiation position determining charged particle beam is switched with the charged particle beam for treatment, and the charged particle beam for treatment is irradiated on the aim position.

Effect of the Invention

As described above, according to the present invention, an effect can be achieved that an aim position of a charged particle beam for treatment can be precisely determine by imaging a subject to observe and diagnosing the subject such as an eye to be inspected while irradiating the position determining charged particle beam on the subject.

BRIEF DESCRIPTION OF DRAWINGS

FIG. 2 is a schematic enlarged view of a film mirror portion according to the exemplary embodiment of the invention.

BEST MODE FOR CARRYING OUT THE INVENTION

An exemplary embodiment of the present invention will be described below in detail with reference to the accompanying drawings. The example is obtained by applying the invention to a particle beam treatment device having a device for determining an aim position of an eyeground.

Example 1

Figure 1:
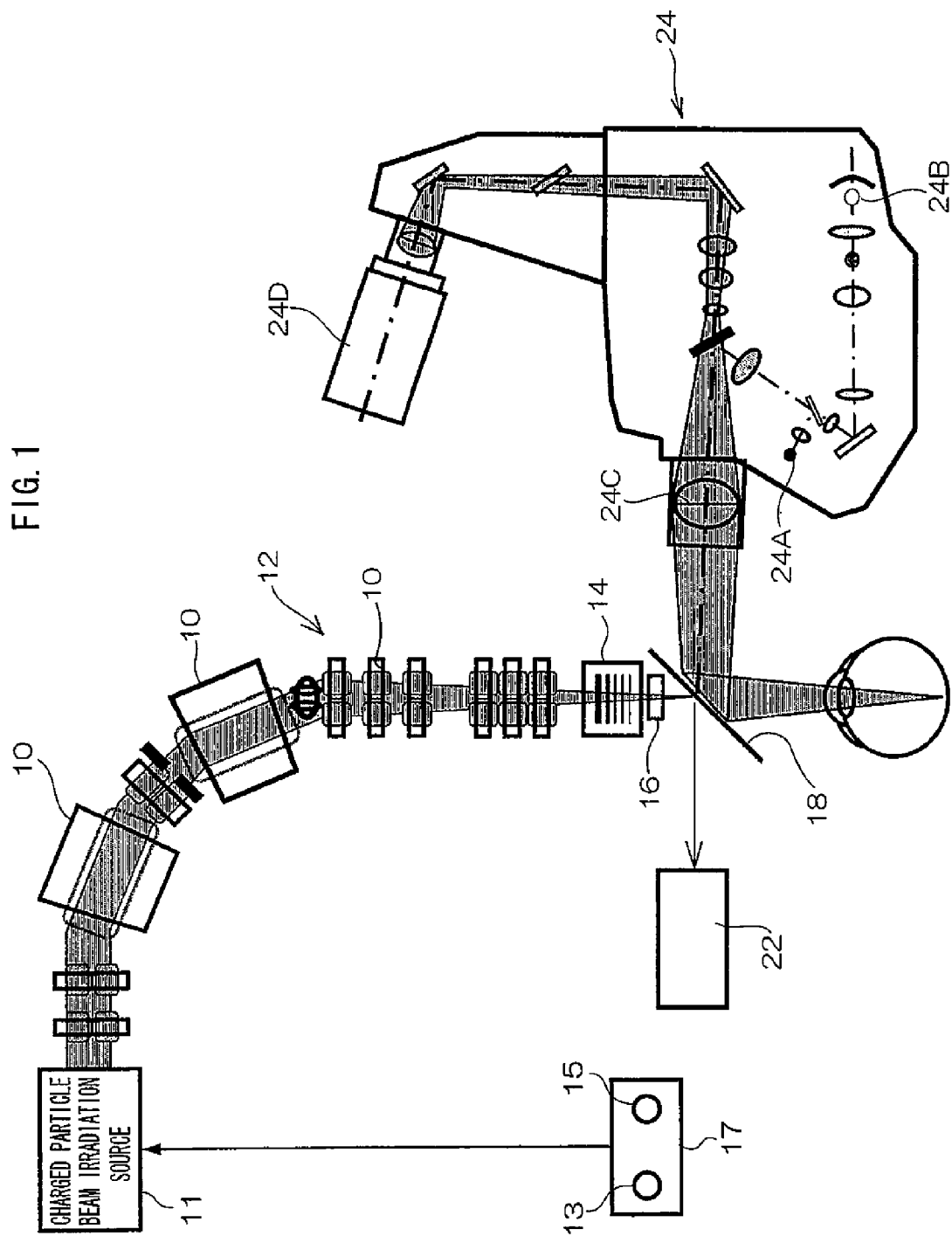
FIG. 1 is a schematic view showing an exemplary embodiment of the present invention.

As shown in FIG. 1, the particle beam treatment device having the eyeground aim position determining device according to the Example is provided with an electromagnet group 12 for deflecting a charged particle beam, in which a plurality of electromagnets 10 which guide a charged particle beam irradiated from a charged particle beam irradiation source 11 toward an eye to be inspected as a subject is arranged. The charged particle beam that may be used includes a heavy ion beam such as a carbon ion beam and a charged particle beam such as a proton beam having a Bragg curve.

Connected to the charged particle beam irradiation source 11 is an operation unit 17 including a switch 13 for starting and stopping irradiation of the charged particle beam and a turn-over switch 15 which switches between a charged particle beam for determining an irradiation position and a charged particle beam for treatment by adjusting an intensity of the charged particle beam.

At an outgoing side of the charged particle beam of the electromagnet group 12 is disposed a range adjuster 14, which, due to a plurality of range shifters that are formed of polymer films and that are arranged in a stack, adjusts a beam irradiation position, in a depth direction of an optic axis of the eye to be inspected, of a charged particle beam irradiated on the eye to be inspected, i.e., adjusts a range of the charge particle beam. The beam irradiation position in the depth direction of the optic axis of the eye, i.e., the irradiation position in an axial direction of the charged particle beam can be adjusted by, for example, several 50 μm increments, by adjusting the number and the thicknesses of the range shifters in the range adjuster 14.

At the charged particle beam outgoing side of the range adjuster 14, a bolus 16 to shape a distribution of the charged particle beam in a plane orthogonal to the axis of the charged particle beam is arranged. By the bolus, the distribution of the charged particle beam is shaped corresponding to the shape or curve of a retina to prevent damage in the retina.

At the charged particle beam outgoing side of the bolus 16, a film mirror 18 consisting of a polymeric material such as polycarbonate or polyethylene terephthalate is arranged at an angle of 45° with respect to the axis of the charged particle beam. As shown in FIG. 2, at a side of the film mirror 18 to which the charged particle beam is irradiated, a light emitter consisting of a luminescent material such as a fluorescent material which emits light due to an irradiation of a charged particle beam is applied to form a scintillator 20. A surface opposite to the surface to which the light emitter of the film mirror 18 is applied functions as a reflecting surface.

In this manner, by applying the light emitter to the film mirror 18, a reflecting unit according to the invention that transmits the charged particle beam, emits light from a region on which the charged particle beam is irradiated, and reflects the light being incident on the reflecting surface toward the outside of the axis of the charged particle beam can be configured.

In the reflecting unit, the scintillator and the mirror may be integrally formed by applying a light emitter on the film mirror as described above. However, a material which can form a reflecting surface may be vapor-deposited on a light emitter member which emits light due to the irradiation of the charged particle beam in order to integrally structure the scintillator and the mirror. Further, the scintillator and the film mirror may be integrally formed by being stuck to each other. When at least one of the scintillator and the mirror is formed of a material which does not transmits a charged particle beam, a hole may be formed in a portion of the member corresponding to an axis of the charged particle beam, so that the charged particle beam partially passes through the hole. The charged particle beam which does not pass through the hole is irradiated on the scintillator and cause the light emitter to emit light.

A material of the member constituting the mirror is not limited to a specific material. However, it is preferable to use a material which does not considerably reduce the energy of the charged particle beam and does not diffuse the charged particle beam.

The example in which the scintillator and the mirror are integrally formed is described above. However, the scintillator and the mirror may be separated from each other and disposed by a predetermined interval in an axial direction of the charged particle beam. Or, it may be formed such that a light emitter is applied to one surface of a single base material, and a material which forms the reflecting surface may be vapor-deposited on the other surface thereof.

At a position where the light emitter of the scintillator 20 may be observed, a beam state observing device 22 having a beam profile monitor formed by a micro-strip gas chamber or the like to monitor a beam profile of the light emitter, and a counter which counts particles of the beam, is disposed. Since the beam state observing device 22 can monitor the beam profile, a position of the charged particle beam on a plane orthogonal to an axis of the charged particle beam irradiated on the eye may be detected.

Further, at a position on which the light reflected from the film mirror 18 may be incident, an eyeground imaging device 24 which images an eyeground of the eye is disposed.

In the eyeground imaging device 24, an excitation light source to irradiate an excitation light on an eyeground is stored. In the Example, a semiconductor laser 24A which irradiates near infrared light and a halogen lamp 24B which irradiates visible light are used as the excitation light source. Any light source which may emit a radiation (ionized or nonionized) to cause a light emission from an eyeground fluorescence contrast agent may be used as the excitation light source.

An objective lens 24C having a focal length in which an eyeground may be focused, and a eyeground (fundus) camera 24D for imaging the eyeground are provided in the eyeground imaging device 24.

Positions of the electromagnet group and the eyeground imaging device are defined in advance such that an optical axis portion of the eyeground imaging device 24 from the film mirror 18 to the eye coincides to a beam axis portion of the charged particle beam from the film mirror 18 to the eye. Therefore, an irradiation position of the charged particle beam substantially coincides to a light irradiation position of the excitation light source.

As an eyeground fluorescence contrast agent, a contrast agent containing fluorescein, indocyanine green, or the like may be used. When the contrast agent containing indocyanine green is used, the excitation light from the semiconductor laser 24A which irradiates near infrared light is used. When the contrast agent containing fluorescein is used, the excitation light from the halogen lamp 24B is used.

Next, a method of treatment by determining an aim position of an eyeground by the particle beam treatment device including the device for determining an aim position of an eyeground according to the exemplary embodiment will be described below. An eyeground fluorescence contrast agent is injected into the eye to be inspected in advance. Further, a charged particle beam is adjusted in advance such that a depth position determining beam having a diameter of about 1 to 10 mm and each irradiation intensity is set to 1% or less of a therapeutic dose.

Figure 3A:
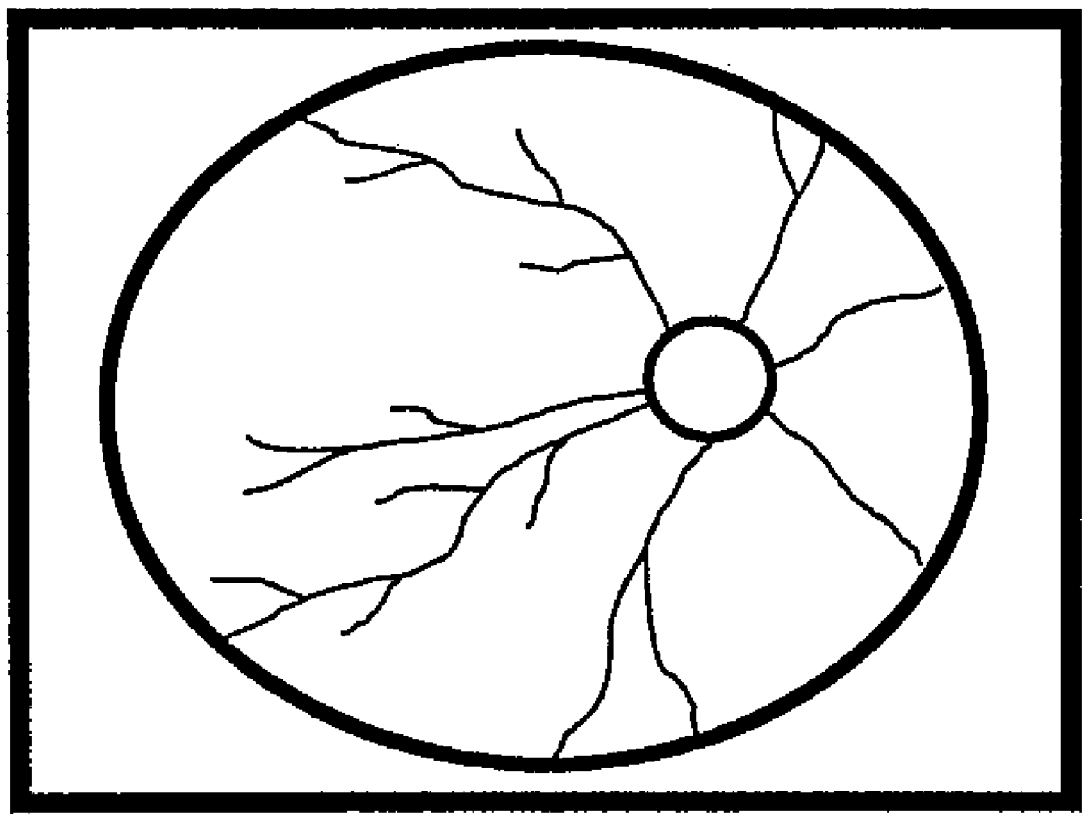
FIG. 3A is a diagram showing a fluorescein fundus angiographic image obtained by an excitation light image.
Figure 3B:
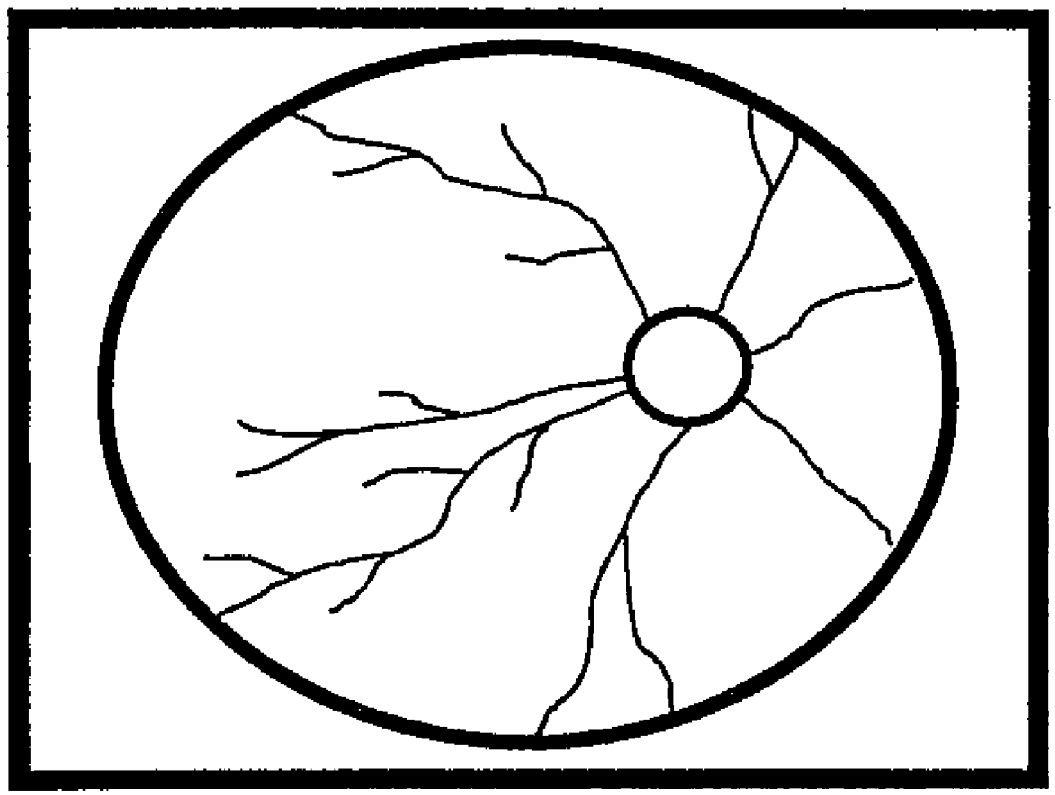
FIG. 3B is a diagram showing a fluorescein fundus angiographic image obtained by preliminary diagnosis.

The device for determining an aim position of an eyeground is arranged immediately in front of the eyeball of the eye, and the excitation light from the excitation light source is irradiated to photograph the eyeground, so that an fluorescein fundus angiographic image (for example, FIG. 3A) obtained by the excitation light is matched with an fluorescein fundus angiographic image (for example, FIG. 3B) obtained in an preliminary diagnosis, and an object to which a treatment irradiation is confirmed.

Further, the depth position determining beam is irradiated on the eye, and position information on a plane orthogonal to the axis of the charged particle beam is acquired by the beam state observing device 22 from the profile of the charged particle beam passing through the light emitter. When the position is offset with respect to a target position, the eye is moved such that the irradiation position of the charged particle beam is adjusted to coincide with the target position on the plane orthogonal to the axis.

After the object of irradiation treatment is confirmed by the matching between the fluorescein fundus angiographic images, while performing multiple-step incremental adjustment of the position of the depth position determining beam in increments of several 50 µm, from the sclera of the eyeground towards the retina, that is, while performing adjustment multiple times for each specific depth, the charged particle beam is irradiated, at each specific depth, to the eyeground, into which the eyeground fluorescence contrast agent is injected. At this time, distortion of a dose distribution of the charged particle beam is compensated by the bolus. Further, in response to the irradiation of the charged particles, luminescence is emitted from the eyeground fluorescence contrast agent containing fluorescein, indocyanine green, or the like.

Figure 3C:
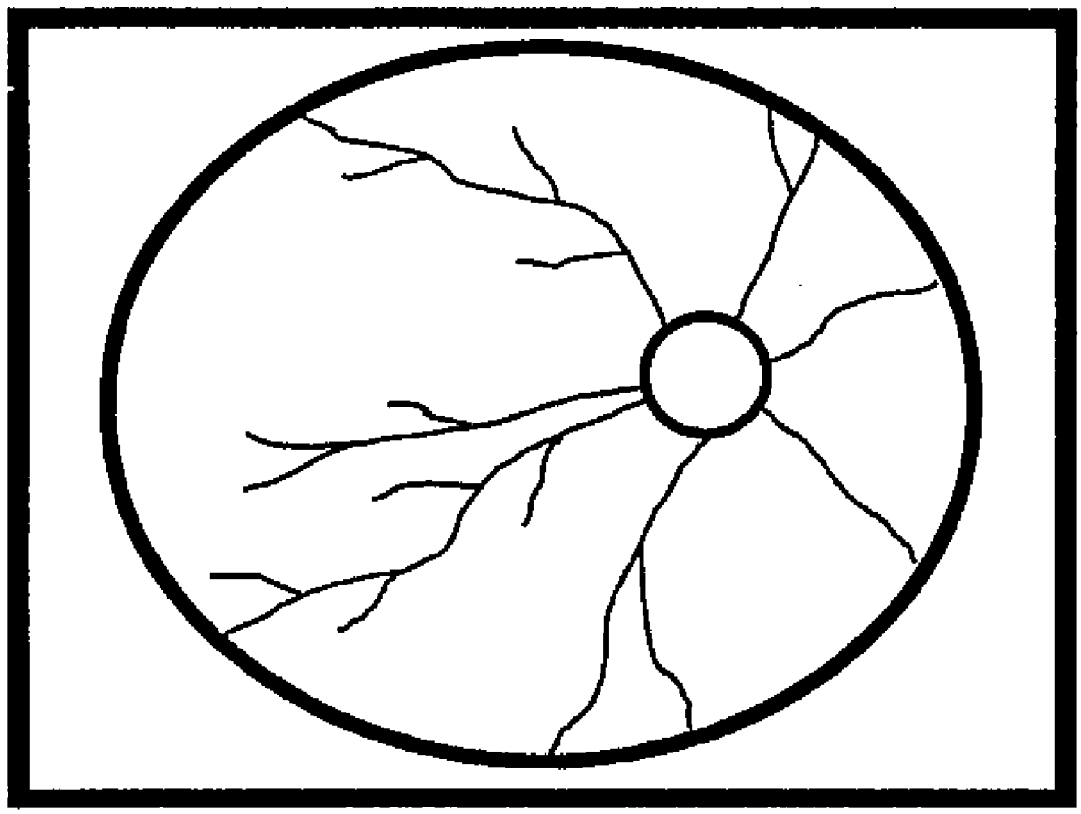
FIG. 3C is a diagram showing a fluorescein fundus angiographic image obtained by an excitation light source.
Figure 3D:
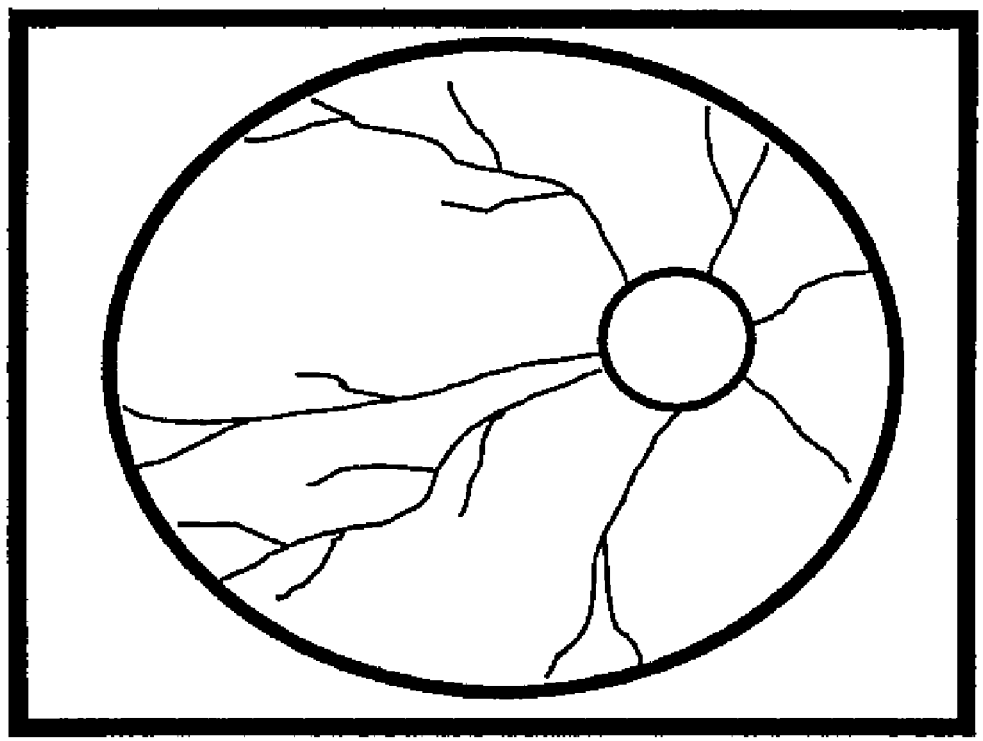
FIG. 3D is a diagram showing a fluorescein fundus angiographic image obtained by a feint beam for depth position determination.

The emission from the eyeground fluorescence contrast agent for every specific depth due to the irradiation of the charged particle beam is reflected by the film mirror 18, incident on the eyeground imaging device having a predetermined operation distance, and an eyeground blood vessel image (for example, an fluorescein fundus angiographic image shown in FIG. 3D) is imaged by the fundus camera. Thus, eyeground blood vessel images for each of the specific depths are obtained. Then, a target eyeground blood vessel image is selected from the plural eyeground blood vessel images, the range adjuster is adjusted to a state of the range adjuster when the selected eyeground blood vessel image is obtained, so that the irradiation depth of the charged particle beam, i.e., the irradiation position may be adjusted to the target position.

Figure 3E:
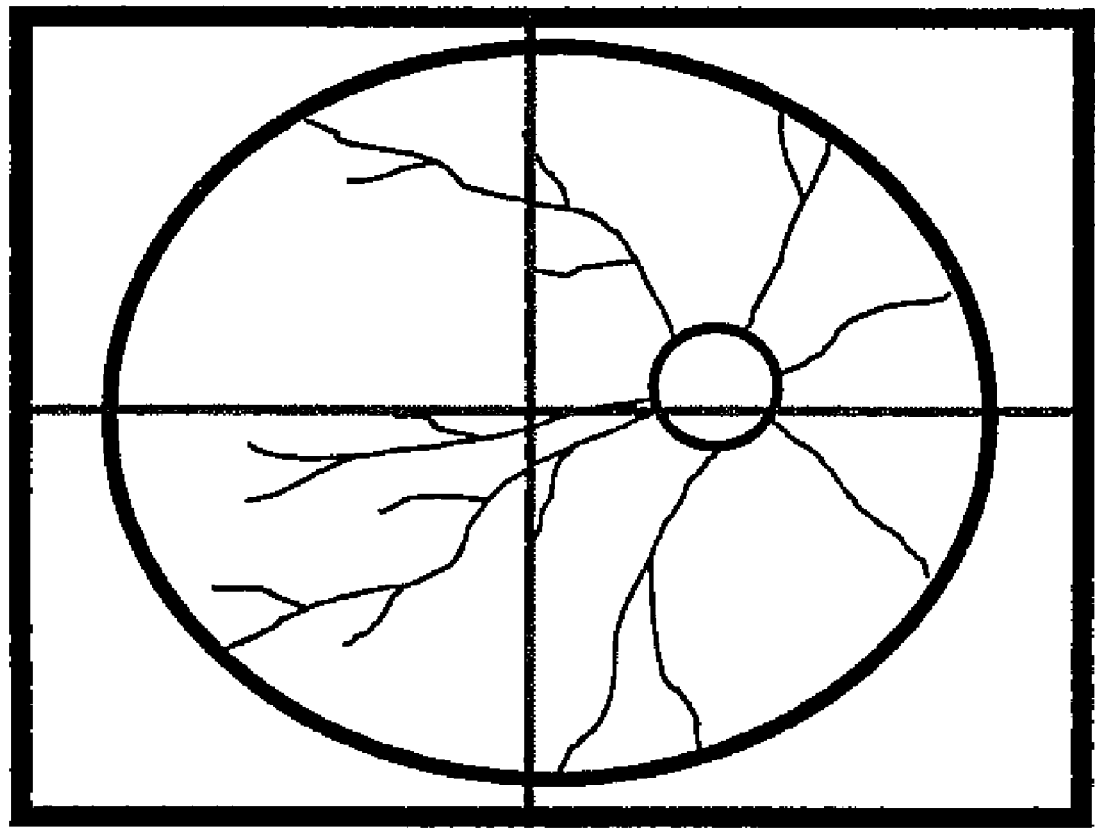
FIG. 3E is a diagram showing a fluorescein fundus angiographic image obtained by an excitation light source.

Subsequently, the turn-over switch 15 of the operation unit 17 is operated to switch the intensity and size of the charged particle beam from those of the depth position determining beam to those a therapeutic beam for treatment, the excitation light is irradiated from the excitation light source of the eyeground imaging device to cause the eyeground fluorescence contrast agent in the eyeground of the eye to emit luminescence, and an image (for example, FIG. 3C) of the eyeground irradiated by the light emission is imaged as a moving image in real time by using the fundus camera. A cross representing an aim to perform treatment irradiation is displayed on the imaged image (FIG. 3E) to determined the aim position of the therapeutic beam, and the therapeutic beam is irradiated. In this manner, the therapeutic beam is irradiated on the aim position indicated by the cross while checking the charged particle beam irradiation position in a planar direction of a focus of decease of the eye to perform treatment.

According to the exemplary embodiment, since a light from the eyeground of the eye is reflected toward the outside of the axis of the charged particle beam, the optical system for eyeground charged particle beam irradiation may be prevented from interfering with the optical system of the eyeground imaging device.

Further, according to the exemplary embodiment, since a charged particle beam can be precisely irradiated on a small region, the invention may be applied to an eyeball (especially, eyeground) disorder in which a charged particle beam is required to be precisely irradiated on a small lesion. Furthermore, the invention may be used as an innovative checking and treatment technique which minimizes an impact on a patient without affecting the patient or the retina of the eye.

In the above description, the eyeground is targeted as a subject. However, treatment using the device according to the invention may be performed to not only the eyeground but other also affected parts.

INDUSTRIAL APPLICABILITY

The invention may be applied to treatment for an affected part by irradiating a charged particle beam such as a carbon ion beam and an excitation light on an eyeground of an eye to be inspected, obtaining an eyeground image to determine an aim position of the charged particle beam, and irradiating a charged particle beam for treatment on the determined aim position.

DESCRIPTION OF REFERENCE NUMERAL AND SIGNS

14 Range adjuster
18 Film mirror
20 Light Emitter
24 Eyeground imaging device

The invention claimed is:
1. A device for determining an aim position of a charged particle beam comprising:
   an adjusting unit that adjusts an irradiation position, in a depth direction of a subject, of an irradiation position determining charged particle beam irradiated from a charged particle beam source;

a reflecting unit that transmits or allows the position determining charged particle beam to pass, and reflects a first emitted light emitted from a region of the subject on which the position determining charged particle beam is irradiated and a second emitted light emitted, due to an irradiation of an excitation light, from a region including the region of the subject on which the position determining charged particle beam is irradiated, toward the outside of the axis of the charged particle beam; and an imaging unit that is arranged at a position where the first emitted light and the second emitted light reflected from the reflecting unit are incident and images the region including the region of the subject on which the position determining charged particle beam is irradiated by allowing incidence of the first emitted light and the second emitted light.

2. The device for determining an aim position of a charged particle beam according to claim 1, further comprising:

a light emitter that is disposed in a path of the position determining charged particle beam irradiated on the subject, and emits light due to the irradiation of the position determining charged particle beam; and a detection unit that detects a position of the charged particle beam irradiated on the subject, on a plane orthogonal to the axis of the charged particle beam, based on the light emitted from the light emitter.

3. The device for determining an aim position of a charged particle beam according to claim 2, wherein the light emitter and the reflecting unit are integrated.

4. The device for determining an aim position of a charged particle beam according to claim 1, wherein a fluorescent contrast agent is injected into the subject.

5. The device for determining an aim position of a charged particle beam according to claim 1, wherein the charged particle beam includes particles having a Bragg peak.

6. A treatment device comprising the device for determining an aim position of a charged particle beam according to claim 1.

7. A device for determining an aim position of a charged particle beam comprising:

an adjusting unit that adjusts an irradiation position, in a depth direction of an optic axis of an eye to be inspected which is a subject, of an irradiation position determining charged particle beam irradiated from a charged particle beam irradiation source;

a reflecting unit that transmits or allows the position determining charged particle beam to pass, and reflects a first emitted light emitted from a region of the eye on which the position determining charged particle beam is irradiated and a second emitted light emitted, due to an irradiation of an excitation light, from a region including the region of the eye on which the position determining charged particle beam is irradiated, toward the outside of the axis of the charged particle beam; and an imaging unit that is arranged at a position where the first emitted light and the second emitted light reflected from the reflecting unit are incident, and images the region including the region of the eye on which the position determining charged particle beam is irradiated by allowing incidence of the first emitted light and the second emitted light.

8. The device for determining an aim position of a charged particle beam according to claim 7, further comprising:

a light emitter that is disposed in a path of the position determining charged particle beam irradiated on the eye, and emits light due to the irradiation of the position determining charged particle beam; and a detection unit that detects a position of the charged particle beam irradiated on the eye on a plane orthogonal to the axis of the beam, based on the emitted light emitted from the light emitter.

9. The device for determining an aim position of a charged particle beam according to claim 8, wherein the light emitter and the reflecting unit are integrated.

10. The device for determining an aim position of a charged particle beam of claim 7, wherein a fluorescence agent is injected into the eye.

11. A method of using the device for determining an aim position of a charged particle beam according to claim 7, the method comprising:

adjusting, by the adjusting unit, in a plurality of steps, an irradiation position along the direction of an optic axis of the eye of the charged particle beam, which is irradiated from the charged particle beam irradiation source, in a direction from the sclera of the eyeground to the retina;

allowing the first emitted light, emitted from the region of the eye on which the position determining charged particle beam is irradiated, to be incident to the imaging unit and imaging, in every step, the region including the region of the eye on which the position determining charged particle beam is irradiated;

adjusting, by the adjusting unit, the irradiation position of the position determining charged particle beam to a target position on the basis of an image obtained by the imaging; and allowing the second emitted light reflected from the reflecting unit to be incident thereon and imaging the region including the region of the eye on which the position determining charged particle beam is irradiated to determine an aim position of a charged particle beam for treatment.

12. The device for determining an aim position of a charged particle beam according to any one of claim 7, wherein the charged particle beam includes particles having a Bragg curve.

13. A treatment device comprising the device for determining an aim position of a charged particle beam according to claim 7.

14. A treatment device using a charged particle beam comprising:

an adjusting unit that adjusts an irradiation position, in a depth direction of a subject, of an irradiation position determining charged particle beam irradiated from a charged particle beam source;

a reflecting unit that transmits or allows the position determining charged particle beam to pass and reflects a first emitted light emitted from a region of the subject on which the position determining charged particle beam is irradiated and a second emitted light emitted, due to an irradiation of an excitation light, from a region including the region of the subject on which the position determining charged particle beam is irradiated, toward the outside of the axis of the charged particle beam; and an imaging unit that is arranged at a position where the first emitted light and the second emitted light reflected from the reflecting unit are incident and images a region including the region of the subject on which the position determining charged particle beam is irradiated by allowing incidence of the first emitted light and the second emitted light, wherein the adjusting unit adjusts, in a plurality of steps, an irradiation position, along a depth direction of a subject, of the position determining charged particle beam irradiated from the charged particle beam irradiation source, the imaging unit images, in every step, a region including the region of the subject on which the position determining charged particle beam is irradiated by allowing the first emitted light emitted from the part of the subject on which the position determining charged particle beam is irradiated to be incident on the imaging unit, the adjusting unit adjusts the irradiation position of the position determining charged particle beam toward a target position on the basis of an image obtained by the imaging, the imaging unit images, by allowing the second emitted light reflected from the reflecting unit to be incident thereon, the region including the region of the subject on which the position determining charged particle beam is irradiated to determine an aim position of a charged particle beam for treatment, and the irradiation position determining charged particle beam is switched with the charged particle beam for treatment, and the charged particle beam for treatment is irradiated on the aim position.

* * * * *